(12) United States Patent
Scheib et al.

(10) Patent No.: US 9,561,029 B2
(45) Date of Patent: Feb. 7, 2017

(54) SURGICAL STAPLER WITH ROLLING ANVIL

(71) Applicant: Ethicon Endo-Surgery, Inc., Cincinnati, OH (US)

(72) Inventors: Charles J. Scheib, Loveland, OH (US); Jeffrey C. Gagel, Loveland, OH (US); Jeffrey S. Swayze, Hamilton, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 747 days.

(21) Appl. No.: 13/967,958

(22) Filed: Aug. 15, 2013

(65) Prior Publication Data

US 2015/0048143 A1    Feb. 19, 2015

(51) Int. Cl.
| | |
|---|---|
| *A61B 17/068* | (2006.01) |
| *A61B 17/064* | (2006.01) |
| *A61B 17/072* | (2006.01) |
| *A61B 17/00* | (2006.01) |
| *A61B 17/32* | (2006.01) |
| *A61B 18/14* | (2006.01) |

(52) U.S. Cl.
CPC ......... *A61B 17/068* (2013.01); *A61B 17/0643* (2013.01); *A61B 17/0644* (2013.01); *A61B 17/07207* (2013.01); *A61B 17/07292* (2013.01); *A61B 17/320092* (2013.01); *A61B 18/1445* (2013.01); *A61B 2017/00398* (2013.01); *A61B 2017/0647* (2013.01); *A61B 2017/07257* (2013.01); *A61B 2017/07278* (2013.01)

(58) Field of Classification Search
CPC ................ A61B 17/068; A61B 17/072; A61B 17/07207; A61B 2017/0488; A61B 2017/07228; A61B 2017/07214; A61B 2017/07257; A61B 2017/07264; A61B 2017/07292; B25C 5/16; B25C 5/1603; B25C 5/1606; B25C 5/1624; B25C 5/1627; B25C 5/1693
USPC ............. 227/175.1–182.1, 19, 120, 136, 135
See application file for complete search history.

(56) References Cited

U.S. PATENT DOCUMENTS

| | | | | |
|---|---|---|---|---|
| 2,296,493 A | * | 9/1942 | Bernstein ............. | B25C 5/0257 227/138 |
| 3,630,428 A | * | 12/1971 | Olney ................... | B25C 5/0207 227/128 |

(Continued)

*Primary Examiner* — Stephen F Gerrity
*Assistant Examiner* — Joshua Kotis
(74) *Attorney, Agent, or Firm* — Frost Brown Todd LLC

(57) ABSTRACT

An apparatus comprises a shaft and an end effector. The end effector is positioned at the distal end of the shaft and is operable to form a fastener assembly to secure tissue. The end effector includes first and second fastener assembly forming features. The first fastener assembly forming feature is rotatable relative to the shaft. The fastener assembly is formed by first and second fastener assembly members. The first fastener assembly member comprises a buttress strip received by the first fastener assembly forming feature. The second fastener assembly member comprises either a wire with protruding portions or a fastener strip with integral protruding fasteners. The buttress strip receives the protruding portions or protruding fasteners to secure tissue between the buttress strip and the wire or fastener strip. The end effector may transect layers of tissue and fasten the layers of tissue together on each side of the transection.

17 Claims, 19 Drawing Sheets

(56) References Cited

U.S. PATENT DOCUMENTS

| | | | |
|---|---|---|---|
| 3,650,453 A * | 3/1972 | Smith, Jr. | A61B 17/0684 227/136 |
| 4,427,008 A * | 1/1984 | Transue | A61B 17/128 227/117 |
| 4,805,823 A | 2/1989 | Rothfuss | |
| 5,415,334 A | 5/1995 | Williamson, IV et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,945,444 B2 | 9/2005 | Gresham et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,240,538 B1 * | 8/2012 | Manoux | A61B 17/07207 227/178.1 |
| 8,317,071 B1 * | 11/2012 | Knodel | A61B 17/07292 227/175.1 |
| 8,317,072 B1 * | 11/2012 | Knodel | A61B 17/07207 227/175.1 |
| 8,397,973 B1 * | 3/2013 | Hausen | A61B 17/064 227/120 |
| 8,403,956 B1 * | 3/2013 | Thompson | A61B 17/072 227/175.1 |
| 8,408,439 B2 | 4/2013 | Huang et al. | |
| 8,453,914 B2 | 6/2013 | Laurent et al. | |
| 8,631,990 B1 * | 1/2014 | Park | A61B 17/0644 227/175.2 |
| 2005/0067454 A1 * | 3/2005 | Vresh | A61B 17/1114 227/19 |
| 2009/0065552 A1 * | 3/2009 | Knodel | A61B 17/072 227/180.1 |
| 2012/0080493 A1 * | 4/2012 | Shelton, IV | A61B 17/064 227/176.1 |

\* cited by examiner

SURGICAL STAPLER WITH ROLLING ANVIL

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. The disclosure of each of the above-cited U.S. patents and U.S. patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
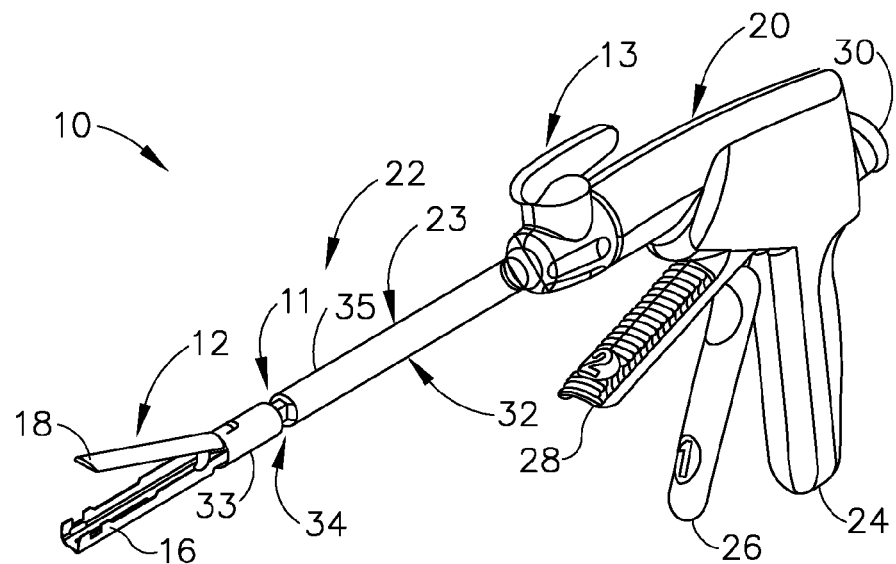
FIG. 1A depicts a perspective view of an exemplary articulating surgical stapling instrument with an end effector in a nonarticulated position.
Figure 1B:
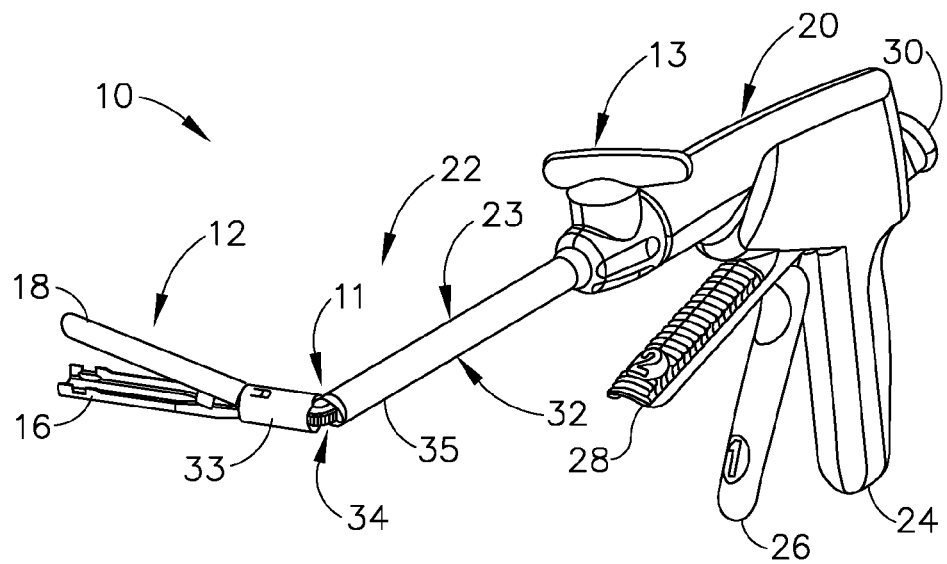
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL STAPLER

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical stapling and severing instrument (10) includes handle portion (20) connected to implement portion (22), the latter further comprising shaft (23) distally terminating in an articulation mechanism (11) and a distally attached end effector (12). Once articulation mechanism (11) and end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal closure ring (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
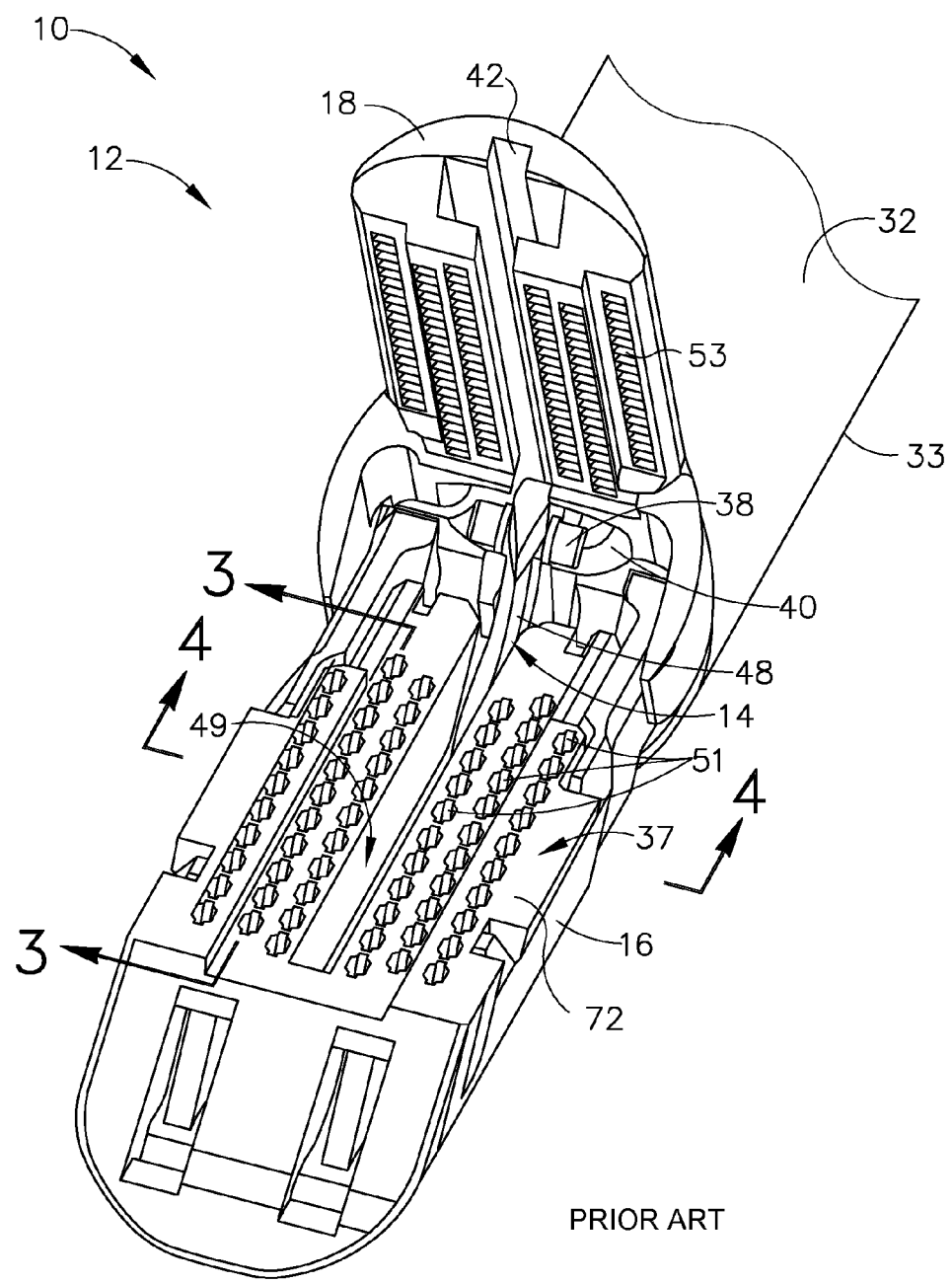
FIG. 2 depicts a perspective view of an opened end effector of the surgical instrument of FIGS. 1A-1B.
Figure 3A:
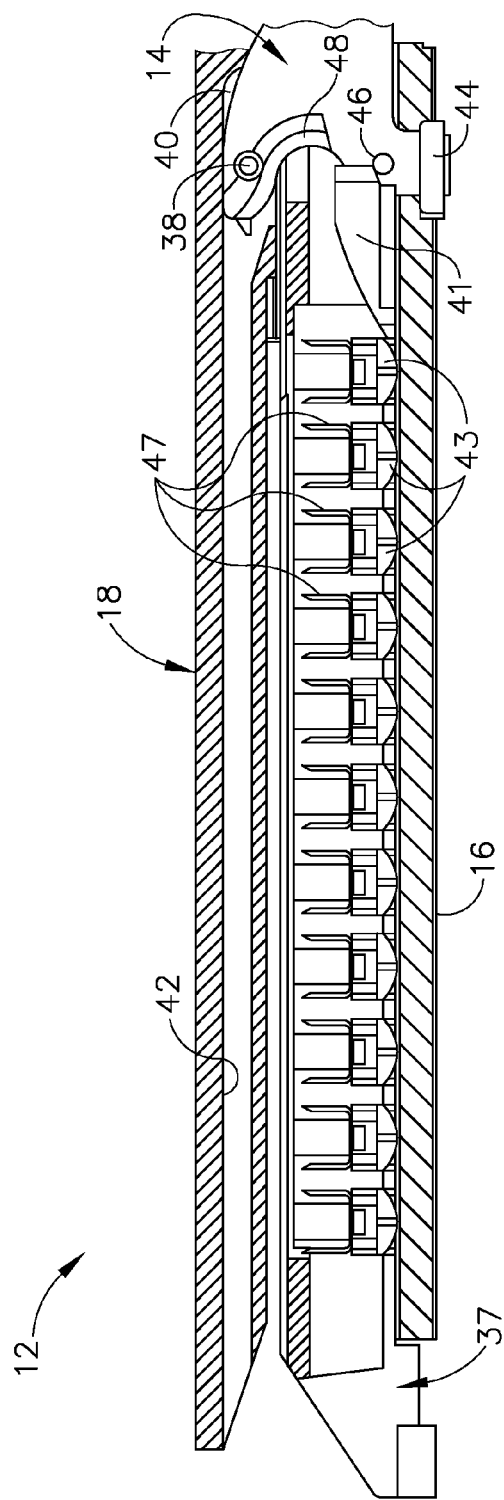
FIG. 3A depicts a side cross-sectional view of the end effector of FIG. 2, taken along line 3-3 of FIG. 2, with the firing bar in a proximal position.
Figure 3B:
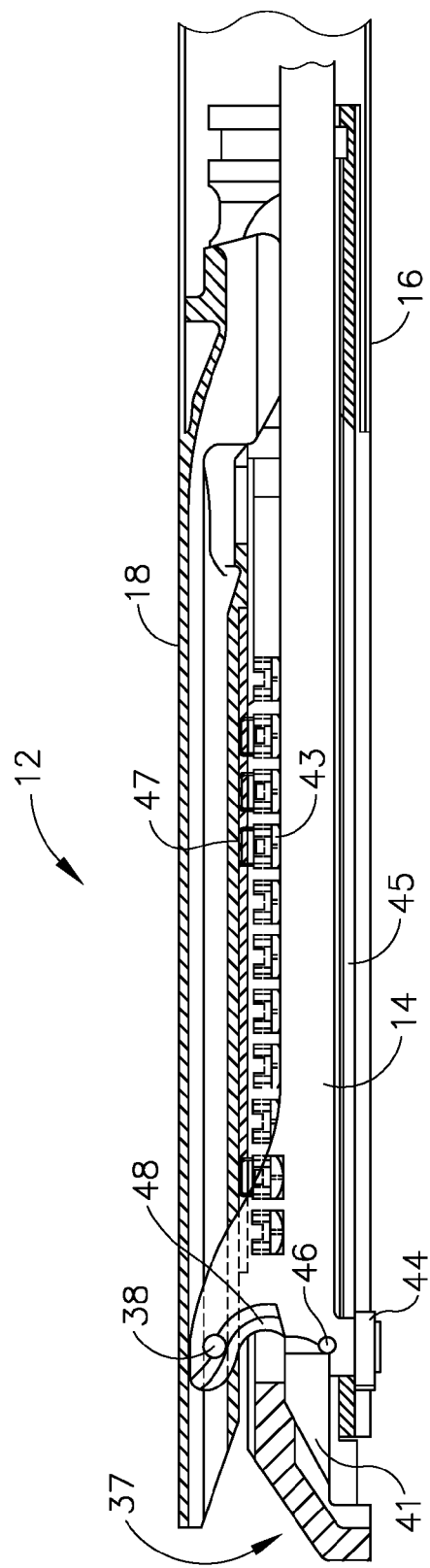
FIG. 3B depicts a side cross-sectional view of the end effector of FIG. 2, taken along line 3-3 of FIG. 2, but showing the firing bar in a distal position.
Figure 4:
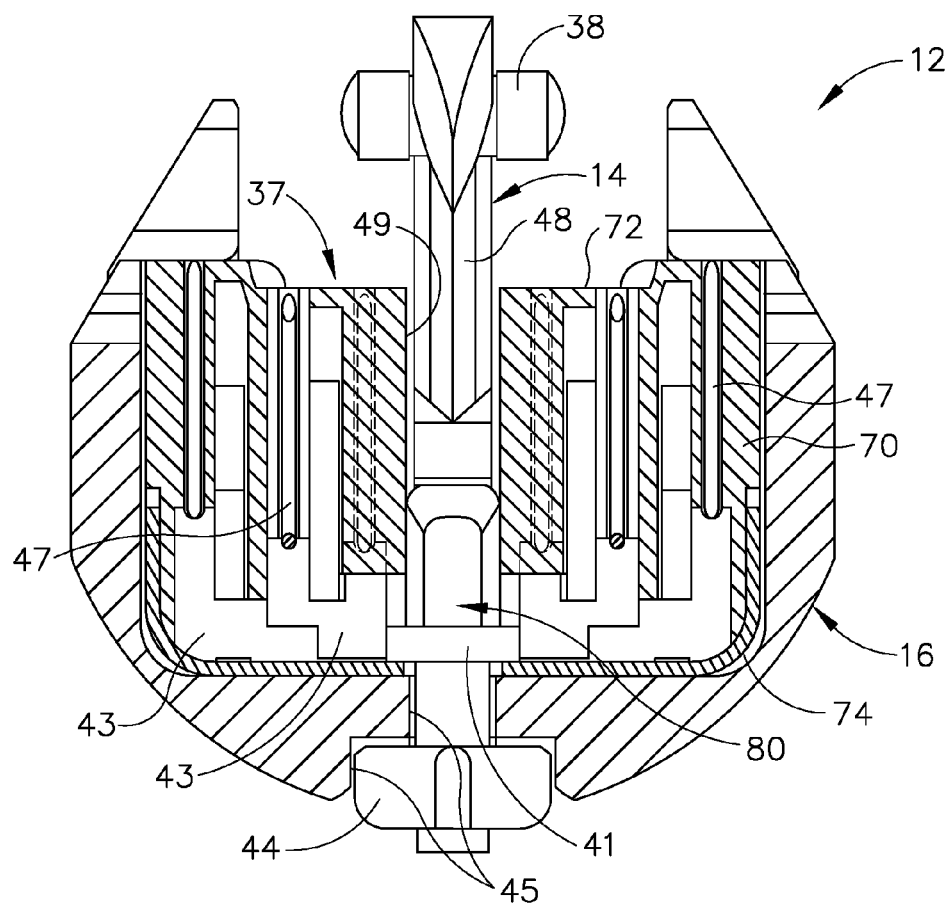
FIG. 4 depicts an end cross-sectional view of the end effector of FIG. 2, taken along line 4-4 of FIG. 2.
Figure 5:
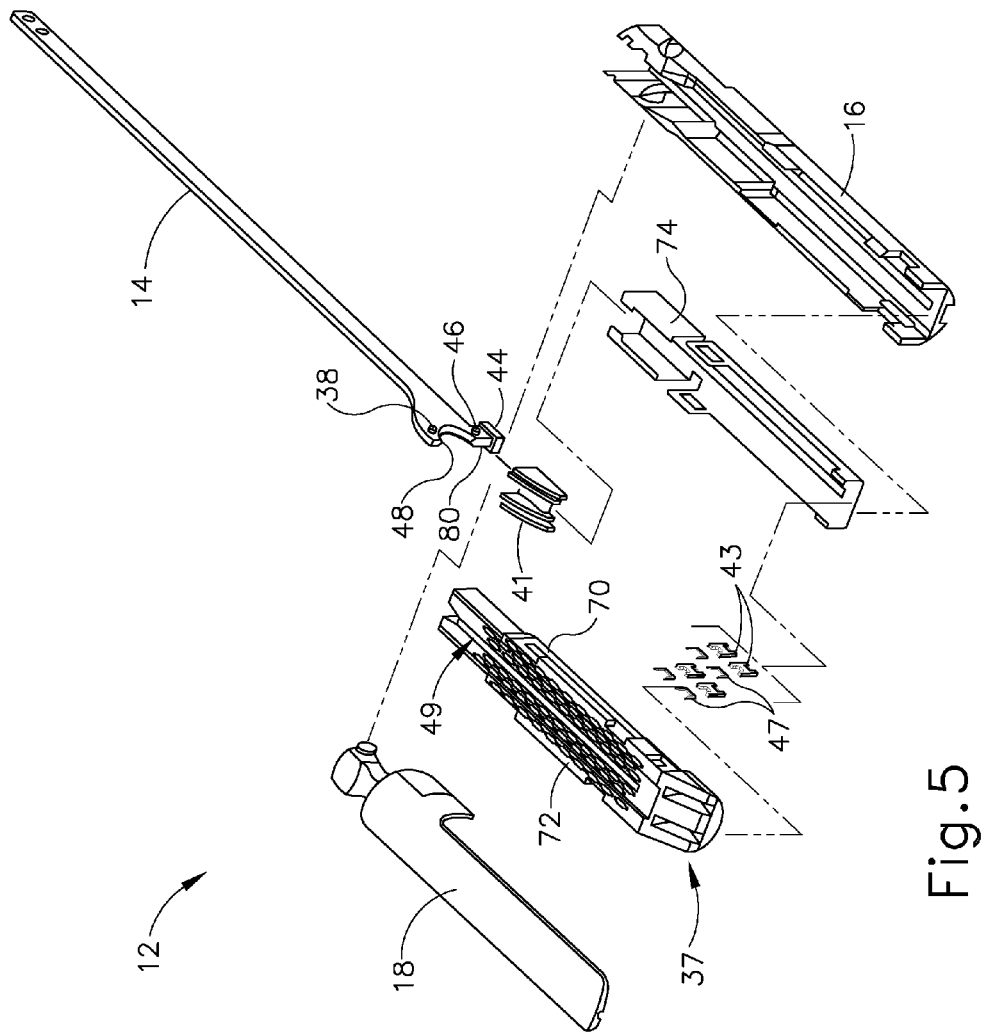
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (72) on one side of vertical slot (49), with another set of three rows of staple apertures (51) being formed through upper deck (72) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into slot (49) within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
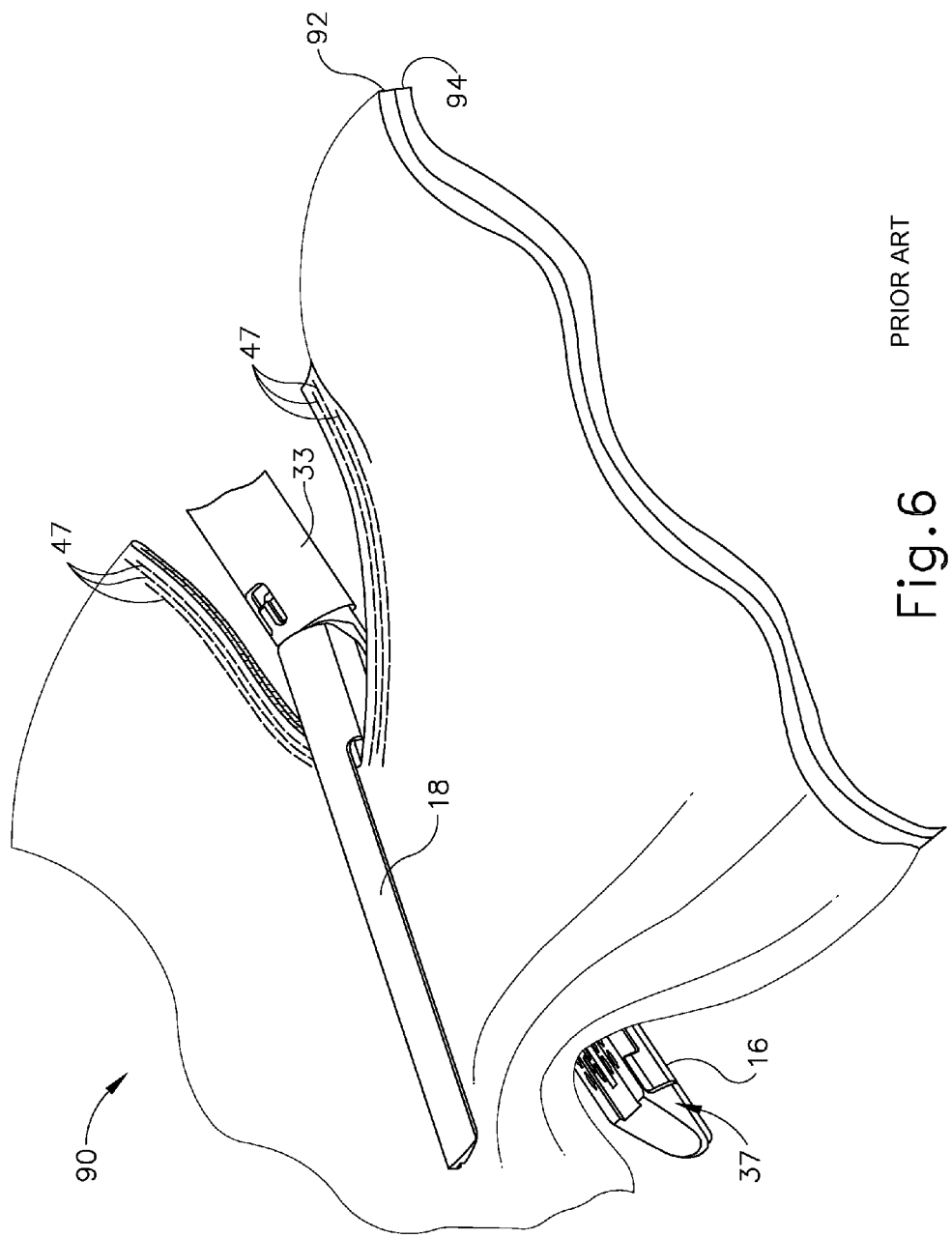
FIG. 6 depicts a perspective view of the end effector of FIG. 2, positioned at tissue and having been actuated once in the tissue.

FIG. 6 shows end effector (12) having been actuated through a single stroke through tissue (90). Cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and/or U.S. Pat. No. 7,721,930.

As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY END EFFECTOR FOR CONTINUOUS STAPLING

It should be understood that the length of tissue transaction achieved during each actuation stroke of instrument (10) is limited by the length of cartridge (37). If the operator wishes to transect tissue along a length greater than the length of cartridge (37), the operator will need to reload instrument (10) with a new cartridge (37). The same principle will apply in the event that the operator wishes to transect tissue in one location in the patient and then transect tissue in another location in the patient—the operator will still need to reload instrument (10) with a new cartridge (37) each time the operator wishes to actuate instrument (10). In some versions the operator will need to remove end effector (12) from the patient to remove the spent cartridge (37) and load a new cartridge (37); then re-insert end effector (12) in the patient. This process may be tedious in some settings. It may therefore be desirable to enable an operator to perform transections (including fasteners along each side of the transaction) along a length greater than that achievable using cartridge (37). Similarly, it may be desirable to enable an operator to perform several transections (including fasteners along each side of each transaction) within a patient using an instrument that does not need to be removed from the patient between each transaction. The various examples described below include variations of instrument (10) that are operable to provide these results. Other variations will be apparent to those of ordinary skill in the art in view of the teachings herein.

A. Exemplary End Effector for Continuous Stapling with Pivoting Jaw and Wire Form Fastener FIGS. 7-12 show an exemplary alternative end effector (100) that may be incorporated into an instrument like instrument (10) discussed above. End effector (100) of this example comprises an upper jaw (110), a lower jaw (120), and a tissue cutting member (130). Upper jaw (110) is pivotable relative to lower jaw (120), such that jaws (110, 120) may be selectively opened and closed to capture tissue. Various suitable ways in which upper jaw (110) may be pivoted relative to lower jaw (120) will be apparent to those of ordinary skill in the art in view of the teachings herein. As will be described in greater detail below, end effector (100)

is operable to transect layers (92, 94) of tissue and fasten the layers (92, 94) of tissue together on each side of the transaction line using a fastening assembly formed by a wire (170) and a buttress strip (160). End effector (100) may thus be used in a manner similar to end effector (12) described above, with the fastening assembly formed by a wire (170) and a buttress strip (160) being similar in effect to formed staples (47) applied by end effector (12). However, it will be understood that end effector (100) of the present example will avoid the need to replace an equivalent of cartridge (37), thus facilitating longer transaction lines and/or a series of transections within a patient without having to repeatedly remove end effector (100) from the patient.

Figure 7:
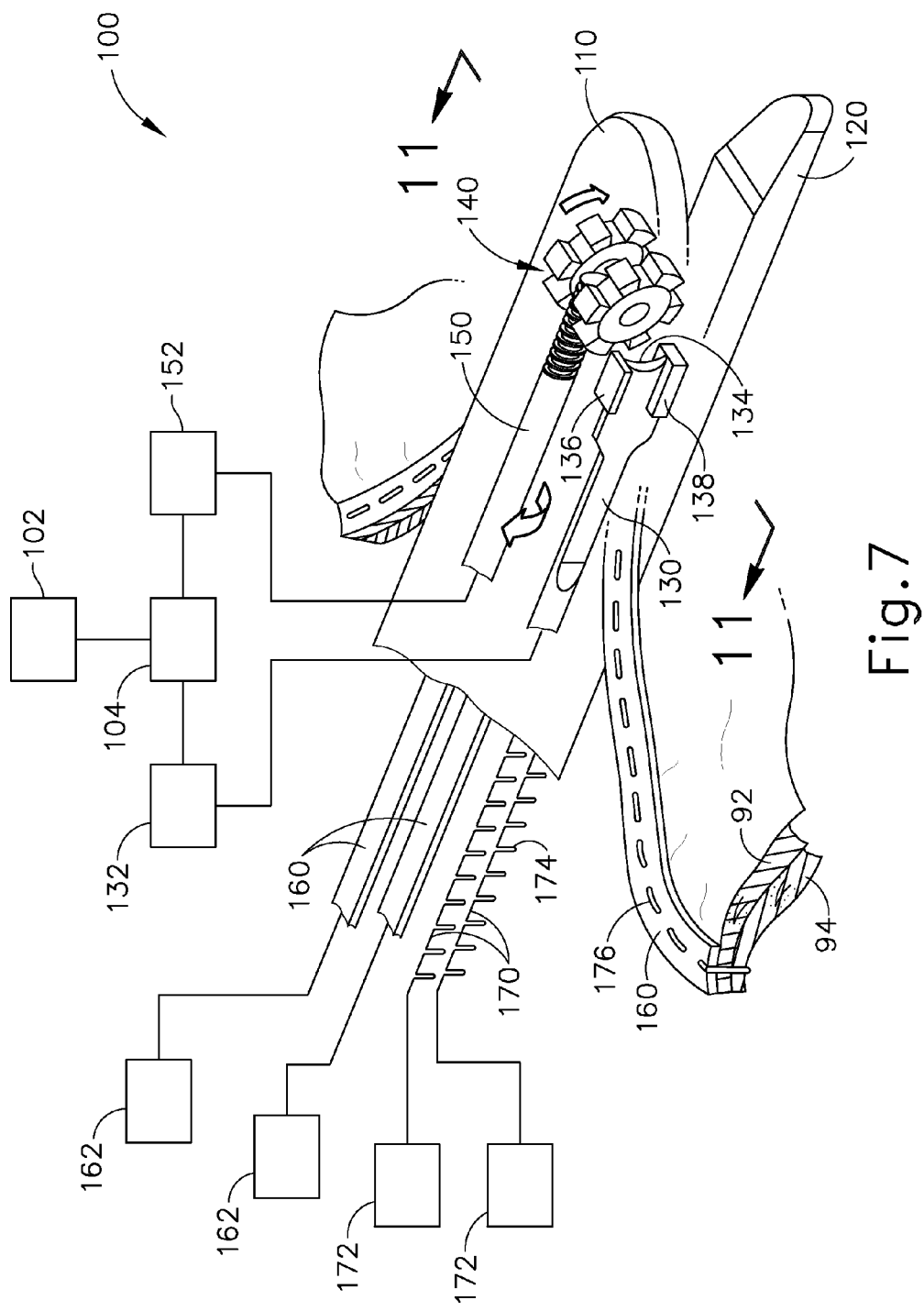
FIG. 7 depicts a schematic view of an exemplary alternative end effector and other components that may be incorporated into the instrument of FIGS. 1A-1B.
Figure 8:
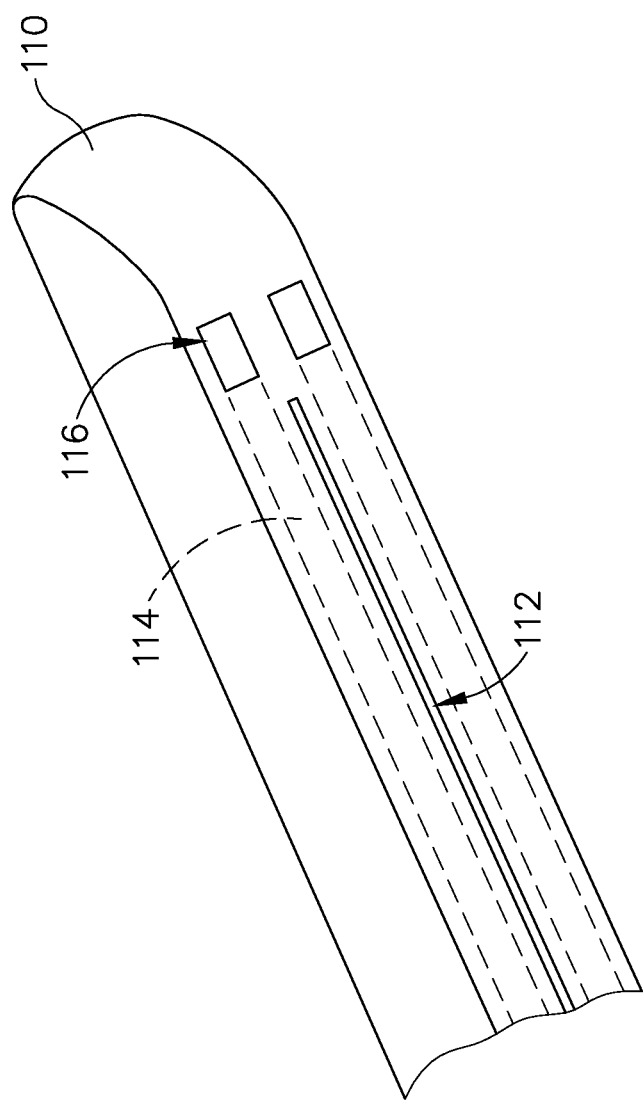
FIG. 8 depicts a partial perspective view of the upper jaw of the end effector of FIG. 7.

As shown in FIG. 7, upper jaw (110) includes a pair of rolling anvils (140) that are driven by a drive shaft (150). Anvils (140) rotate about an axis that is perpendicular to the longitudinal axis of end effector (150); while drive shaft (150) rotates about an axis that is parallel to the longitudinal axis of end effector (150). Anvils (140) rotate together simultaneously in the same direction. Various suitable transmission configurations that may be used to couple drive shaft (150) with anvils (140) will be apparent to those of ordinary skill in the art in view of the teachings herein. Drive shaft (150) is coupled with a rotary drive source (152), which may include a motor and/or any other suitable kind of rotary drive source (152). As shown in FIG. 8, upper jaw (110) defines a slot (112) that is configured to slidably receive tissue cutting member (130). Upper jaw (110) also defines a pair of channels (114) and openings (116) on each side of slot (112). Openings (116) are positioned to expose portions of anvils (140). In particular, openings (116) are configured to receive protruding portions (174) of wire (170) to enable anvils (140) to form the fastening assembly as will be described in greater detail below.

Figure 12:
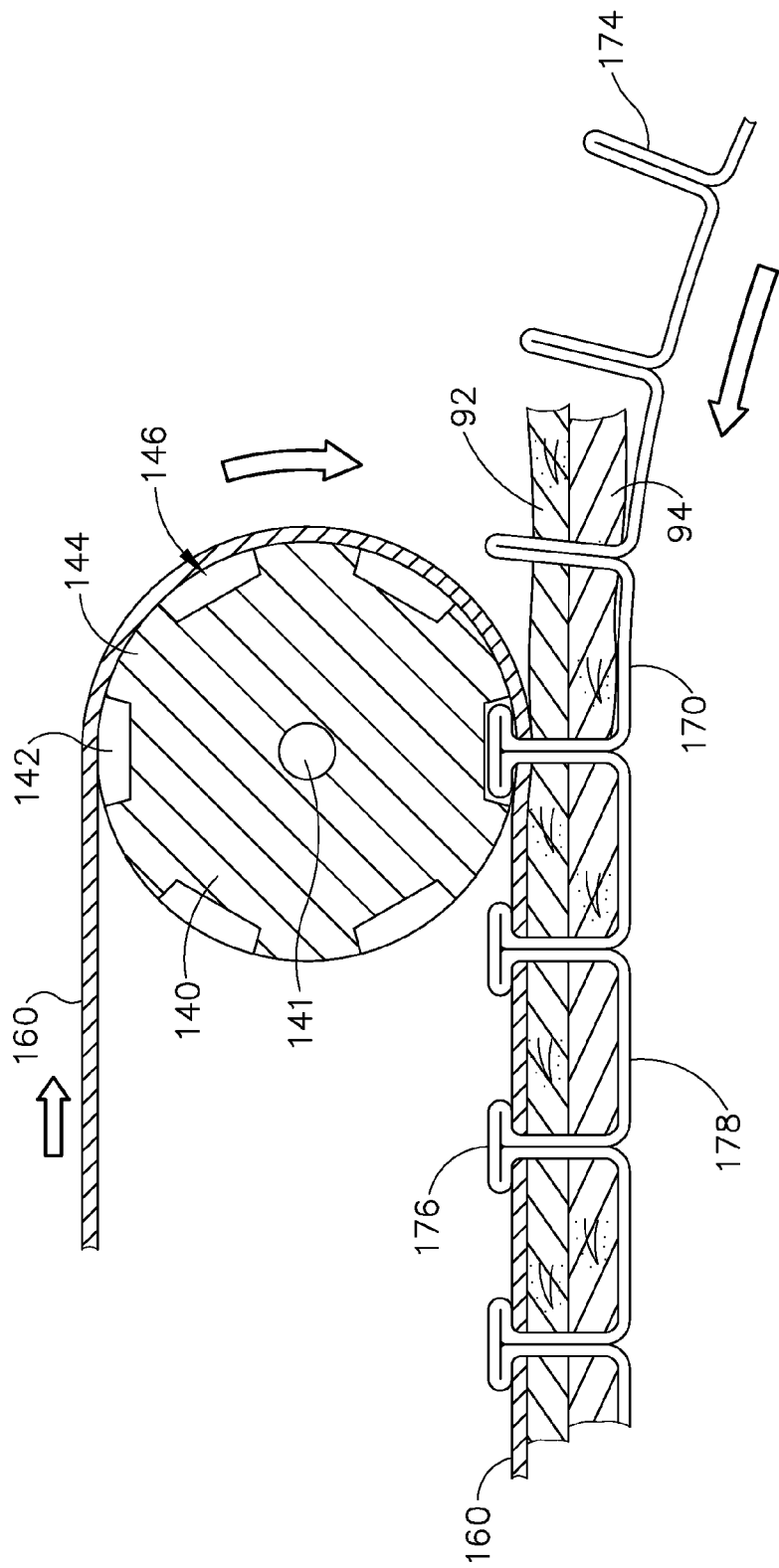
FIG. 12 depicts a cross-sectional side view of the end effector of FIG. 7, taken along line 12-12 of FIG. 11.

As shown in FIG. 12, each anvil (140) includes radially extending flanges (142) and forming chamber sidewalls (144), which cooperate to form a series of forming chamber recesses (146) about the perimeter of anvil (140). While six recesses (146) are shown in the present example, it should be understood that any other suitable number of recesses (146) may be used. As will be described in greater detail below, recesses (146) are configured to receive buttress strip (160) and protruding portions (174) of wire (170). Recesses (146) are further configured to deform protruding portions (174) of wire (170) to produce formed portions (176) of wire (170). Each anvil (140) also defines a bore (148) that is configured to receive an axle (141). Axle (141) is driven by drive shaft (150) as noted above. While both anvils (140) share a common axle (141) in the present example, some other versions may provide separate axles (141) for anvils (140).

Buttress strips (160) of the present example are fed over the top of anvils (140) as shown in FIG. 12. Buttress strips (160) may be formed of any suitable material(s), including but not limited to the following: a polyglutamic acid (PGA) polymer; polyglycolic acid:Trimethylene carbonate (PGA: TMC); bovine pericardium; compressible hemostat material such as, for example, oxidized regenerated cellulose (ORC) or a bioabsorbable foam (e.g., compressed into sheet form); polydioxanone (PDS); polyglycerol sebacate (PGS); polyglycolic acid (PGA); polycaprolactone (PCL); polylactic acid (PLA); polyhydroxyalkanoate (PHA); poliglecaprone (PGCL); polylactic acid (PLA or PLLA); polyhydroxyalkanoate (PHA); polycaprolactone (PCL); polyurethane; polypropylene (PP); polyethylene (PE); polycarbonate; polyamides, such as nylon, polyvinylchloride (PVC), polymethylmethacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, silicons, and combinations of any of the foregoing materials. Furthermore, buttress strips (160) may be formed of foamed elastomers and/or porous elastomers, such as, for example, silicone, polyisoprene, expanded polytetrafluoroethylene (ePTFE), co-polyetherester urethane foam, and/or any other suitable material(s). Various other suitable materials and configurations that may be used for buttress strips (160) will be apparent to those of ordinary skill in the art in view of the teachings herein.

Each anvil (140) receives a respective buttress strip (160). In some versions, anvils (140) include protrusions and buttress strips (160) include openings that cooperate with the protrusions of anvils (140) to provide a tractor feed configuration, such that anvils (140) directly pull buttress strips (160) distally when anvils rotate (140). Other suitable ways in which buttress strips (160) may be advanced distally will be apparent to those of ordinary skill in the art in view of the teachings herein. In the present example, each buttress strip (160) is released from a respective spool or reel (162). Reels (162) may be located within a handle portion like handle portion (20) and/or in any other suitable location. Reels (162) may be configured to freely release buttress strips (160) as buttress strips (160) are pulled distally and/or reels (162) may include features that selectively lock/unlock the release of buttress strips (160) from reels (162). In some versions, reels (162) are powered to rotate and thereby actively feed buttress strips (160).

Figure 11:
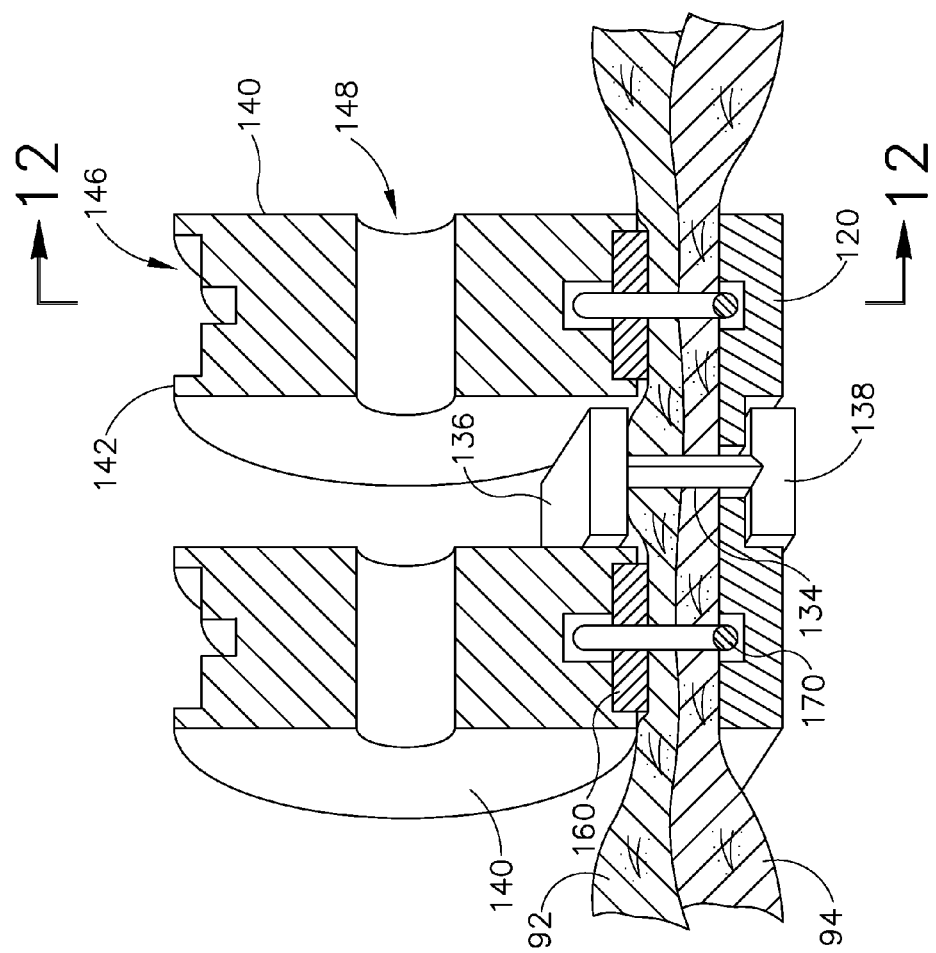
FIG. 11 depicts a cross-sectional end view of the end effector of FIG. 7, taken along line 11-11 of FIG. 7.

As best seen in FIGS. 11-12 and as will be described in greater detail below, buttress strips (160) are configured to receive respective protruding portions (174) of wire (170) as protruding portions (174) enter recesses (146). Buttress strips (160) may include preformed openings that facilitate passage of protruding portions (174) through buttress strips (160). Alternatively, protruding portions (174) may simply pierce or otherwise penetrate buttress strips (160) as protruding portions (174) enter recesses (146).

Figure 9:
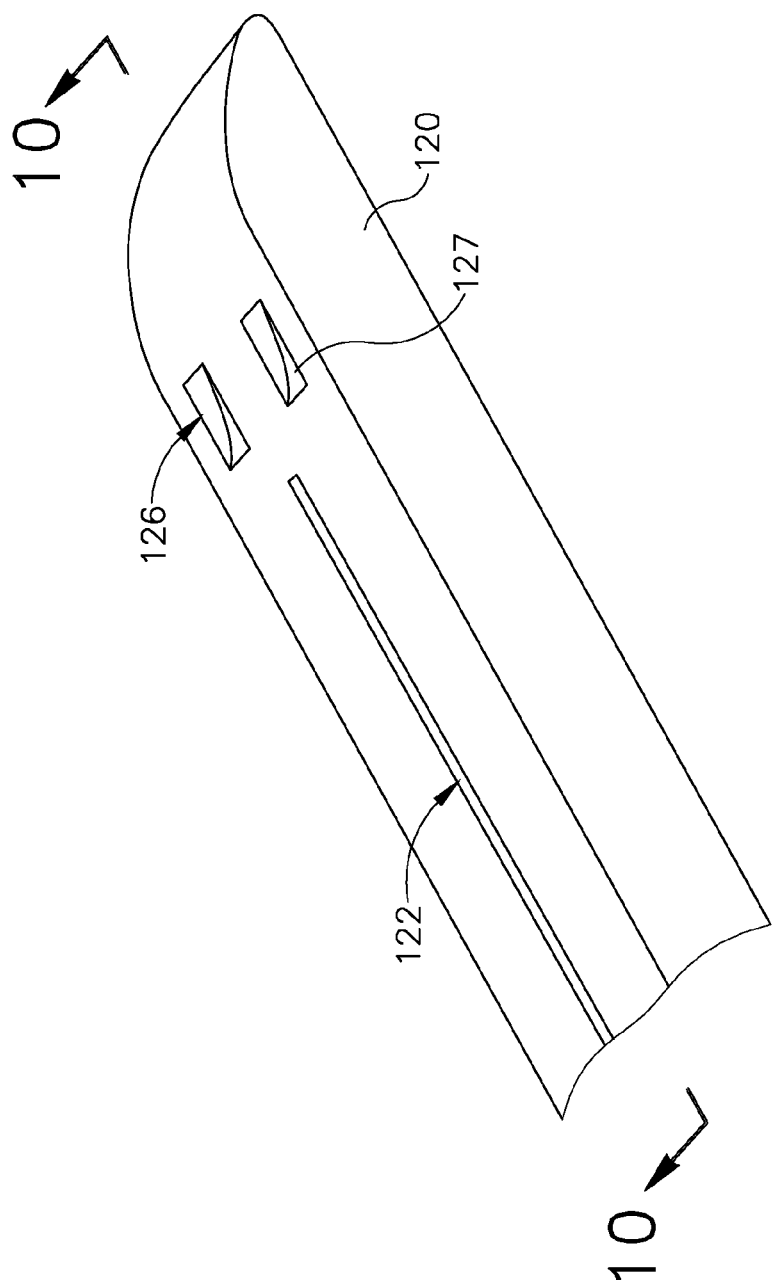
FIG. 9 depicts a partial perspective view of the lower jaw of the end effector of FIG. 7.
Figure 10:
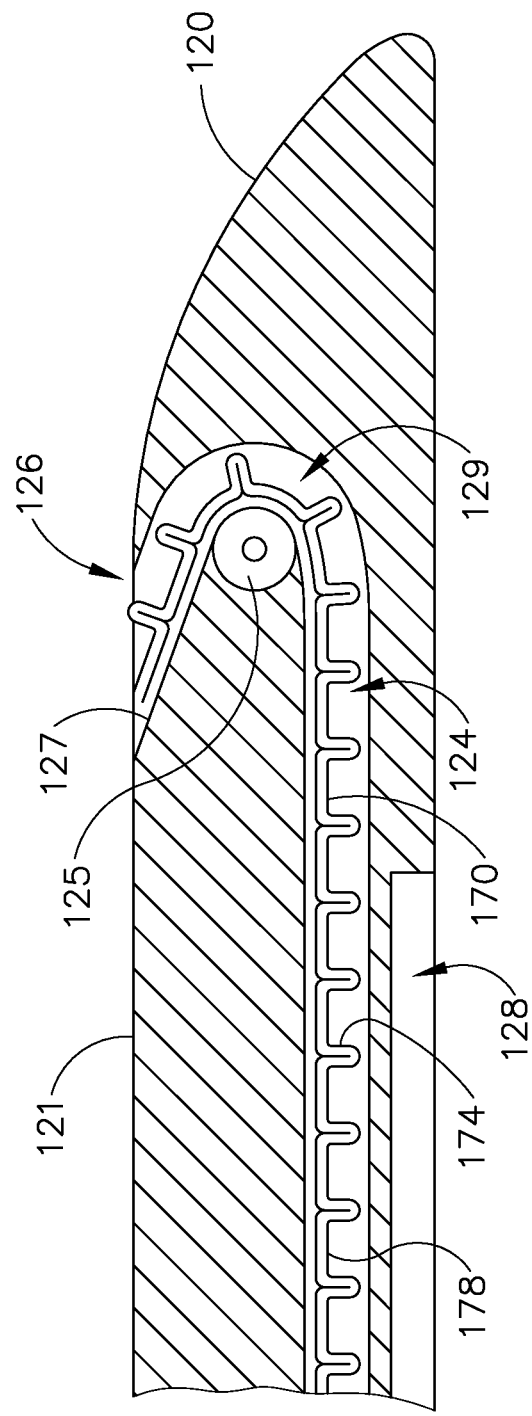
FIG. 10 depicts a side cross-sectional view of the lower jaw of FIG. 9, taken along line 10-10 of FIG. 9.

As shown in FIG. 9, lower law (120) defines a slot (122) that is configured to slidably receive tissue cutting member (130). Lower jaw (120) also defines a pair of channels (124) that terminate at openings (126) on each side of slot (122). Openings (126) are positioned to align with openings (116) of upper jaw (110) when upper law (110) is in a closed position relative to lower jaw (120). As best seen in FIG. 10, channel (124) is sized to receive wire (170). In particular, channel (124) is configured to enable communication of wire (170) distally through lower jaw (120), without causing interference with protruding portions (174). Channel (124) further includes a redirection zone (129) configured to redirect the travel of wire (170) from a distal direction to a proximal direction as wire (170) approaches the distal end of lower jaw (120). A roller (125) is positioned at redirection zone (129) and rotates freely relative to lower jaw (120), thereby reducing friction between wire (170) and lower jaw (120) at redirection zone (129). Of course, roller (125) is merely optional. The terminal end of each channel (124) includes a ramp (127) adjacent to opening (126). Each ramp (127) defines a shallow obtuse angle relative to the upper deck surface (121) of lower jaw (120), enabling wires (170) to exit openings (126) along paths that are nearly parallel to the upper deck surface (121) of lower jaw (120). Various suitable angles for ramps (127) will be apparent to those of ordinary skill in the art in view of the teachings herein.

As noted above, each wire (170) includes a plurality of transversely protruding portions (174). Protruding portions (174) are separated by base lengths (178) of wire (170). Wire (170) is malleable such that formed portions (176) will substantially maintain their shape once formed. Wire (170) may be formed of various kinds of metal and/or any other suitable kind of material(s). Protruding portions (174) are configured to penetrate layers of tissue (92, 94) as shown in FIG. 12. In some versions, protruding portions (174) are sharpened to facilitate tissue penetration, though such sharpening is not necessarily required. While wire (170) has enough flexibility to enable formation of formed portions (176) by anvils (140), wire (170) has enough rigidity for protruding portions (174) to substantially maintain their configuration while protruding portions (174) penetrate tissue. Various suitable materials and configurations that may be used for forming wire (170) will be apparent to those of ordinary skill in the art in view of the teachings herein. In the present example, each wire (170) is released from a respective spool or reel (172). Reels (172) may be located within a handle portion like handle portion (20) and/or in any other suitable location. Reels (172) may be configured to freely release wires (170) as wires (170) are pulled distally and/or reels (172) may include features that selectively lock/unlock the release of wires (170) from reels (172). In some versions, reels (172) are powered to rotate and thereby actively feed wire (170).

Tissue cutting member (130) is similar to firing bar (14) described above in that tissue cutting member (130) has a distal cutting edge (134) that is configured to sever tissue captured between jaws (110, 120). In some versions, tissue cutting member (130) is operable to drive upper jaw (110) toward lower jaw (120) as tissue cutting member (130) is advanced distally. In some other versions, upper jaw (110) is driven toward lower jaw by a separate feature (e.g., a feature similar to closure sleeve (32), etc.). As best seen in FIG. 7, tissue cutting member (130) of the present example comprises an upper flange (136) and a lower flange (138) at the top and bottom, respectively, of distal cutting edge (134). Lower flange (138) is slidably disposed in a channel (128) formed in lower jaw (120) as shown in FIG. 10); while upper flange (136) is slidably disposed in a channel (not shown) formed in upper jaw (110). Distal cutting edge (134) is slidably disposed in slots (112, 122) of jaws (110, 120). Tissue cutting member (130) is in communication with a drive assembly (132), which is operable to drive tissue cutting member distally through slots (112, 122) in jaws (110, 120).

In the present example, drive assembly (132) includes a motor. In some versions, rotary drive source (152) and drive assembly (132) are driven by the same, common motor. Various suitable features that may be used to convert activation of a motor into translation of tissue cutting member (130) will be apparent to those of ordinary skill in the art in view of the teachings herein. In some other versions, drive assembly (132) may include a manual mechanical drive train that is actuated by a user input like firing trigger (28) described above. Regardless of whether tissue cutting member (130) is advanced by motor or manually, some versions of tissue cutting member (130) are operable to vibrate at an ultrasonic frequency (e.g., approximately 55.5 kHz) to simultaneously sever tissue and denature the proteins in adjacent tissue cells, thereby providing a coagulative effect with relatively little thermal spread. It should therefore be understood that drive assembly (132) may include one or more piezoelectric elements that are operable to convert electrical power into ultrasonic vibrations. As yet another merely illustrative example, tissue cutting member (130) may be selectively activated with RF energy. In some such versions, one or more other features of end effector (100) provides a return path for such RF energy, such that end effector (100) operates as a biopolar electrosurgical end effector. In some other versions, a ground pad is placed on or under the patient, such that end effector (100) operates as a monopolar electrosurgical end effector.

As shown in FIG. 7, drive assembly (132) and rotary drive source (152) are both coupled with a control module (104), which is further coupled with a power source (102). Control module (104) is operable to selectively provide power from power source (102) to drive assembly (132) and/or rotary drive source (152) based on user input and/or based on other information. By way of example only, control module (104) may include one or more switches that are in communication with a user input (e.g., firing trigger (28), etc.), that thereby selectively complete a circuit between the user input, drive assembly (132), rotary drive source (152), and power source (102). In addition or in the alternative, control module (104) may be in communication with one or more sensors (e.g., encoder wheel, reed switch(es), tissue contacting electrodes, etc.) that are operable to detect an operational parameter associated with end effector (100) (e.g., the presence of tissue between jaws (110, 120), etc.) and control activation of rotary drive source (152) and/or power source (102) based on such information. Various suitable configurations for control module (104), inputs that may be processed by control module (104), and results of such processing will be apparent to those of ordinary skill in the art in view of the teachings herein. It should also be understood that power source (102) may comprise a battery (e.g, located within handle portion (20), etc.), an external power source (e.g., coupled with handle portion (20) via cable), and/or some other kind of power source (102). Alternatively, power source (102) may be eliminated. For instance, all of the operation of end effector (100) may be driven manually by the hand of the operator.

In an exemplary use, the operator may position layers (92, 94) of tissue between jaws (110, 120), then drive upper jaw (110) toward lower jaw (120) to clamp the layers (92, 94) of tissue between jaws (110, 120). The operator may then actuate rotary drive source (152) to rotate anvils (140). This rotation of anvils (140) pulls buttress strips (160) distally and around anvils (140). The rotation of anvils (140) also pulls wires (170) distally around rollers (125). This action eventually drives buttress strips (160) and wires (170) proximally, with protruding portions (174) of wire (170) penetrating through the underside of layers (92, 94) while buttress strip (160) is applied in apposition with the upper side of layers (92, 94) as best in FIG. 12. After further penetrating buttress strips (160), protruding portions (174) of wire (170) encounter anvils (140), which deform protruding portions (174) to form formed portions (176) of wire (170) on the upper side of buttress strip (160). Formed portions (176) act as rivet heads, preventing wire (170) from being pulled back through buttress strip (160) and the layers (92, 94) of tissue underneath buttress strip (160). The base lengths (178) of wire (170) further secure wire (170) to the underside of tissue layers (92, 94). Thus, the formed wire (170) and buttress strip (160) cooperate to secure the layers (92, 94) of tissue together.

Before, during, and/or after the layers (92, 94) of tissue are secured by formed wire (170) and buttress strip (160), tissue cutting member (130) may be actuated to sever the tissue. In particular, tissue cutting member (130) may transect the layers (92, 94) tissue along a path that is parallel to and between the fastener assemblies formed by wire (170) and buttress strip (160). The net result may look similar to what is shown in FIG. 7, where the fastener assemblies formed by wire (170) and buttress strip (160) are positioned adjacent to the tissue transaction created by tissue cutting member (130). In the present example, slots (112, 122) distally terminate proximal to openings (116, 126), such that tissue cutting member (130) does not travel distally to the point where layers (92, 94) of tissue are fastened by wire (170) and buttress strip (160). This may ensure that the layers (92, 94) of tissue are fastened before the layers (92, 94) of tissue are transected. In addition or in the alternative, drive assembly (132) may be manually and/or automatically controlled to ensure proper timing of tissue cutting member (130) actuation (e.g., in relation to fastening by wire (170) and buttress strip (160) and/or otherwise).

It should be understood that the fastener assemblies formed by wire (170) and buttress strip (160) may provide anchoring of layers (92, 94) of tissue and may also provide hemostasis at the transection edges created by tissue cutting member (130). Hemostasis may be further enhanced if jaws (110, 120) are used to substantially compress the layers (92, 94) of tissue when the fastener assembly is deployed. It should also be understood that the above process may be carried out and repeated for as long as desired, enabling the operator to create secured transections having an effectively indefinite length (e.g., especially if a significant amount of buttress strip (160) and wire (170) is preloaded), without having to remove end effector (100) from the patient. Similarly, the above process may be repeated to create several separate secured transections within the patient, without having to remove end effector (100) from the patient. In instances where the operator is moving from one transection site to another transection site, the operator may simply use a conventional cutting instrument to cut wire (170) and/or buttress strip (160) before moving to the latter transection site.

In some variations, end effector (100) includes a feature enabling selective adjustment of the gap distance between closed jaws (110, 120), which may effectively vary the height of the fasteners ultimately formed by wire (170). Such adjustability may be desired to account for varying tissue thicknesses. Various suitable ways in which selective adjustment of the gap distance between closed jaws (110, 120) may be provided will be apparent to those of ordinary skill in the art in view of the teachings herein. As yet another merely illustrative variation, end effector (100) may enable adjustment of the distance between axle (141) and the lower surface of upper jaw (110), which may effectively vary the height of fasteners ultimately formed by wire (170). It should also be understood that gap adjustment and/or fastener height adjustment may not be required. Other variations for the construction, use, and operability of end effector (100) will be apparent to those of ordinary skill in the art in view of the teachings herein.

Figure 13:
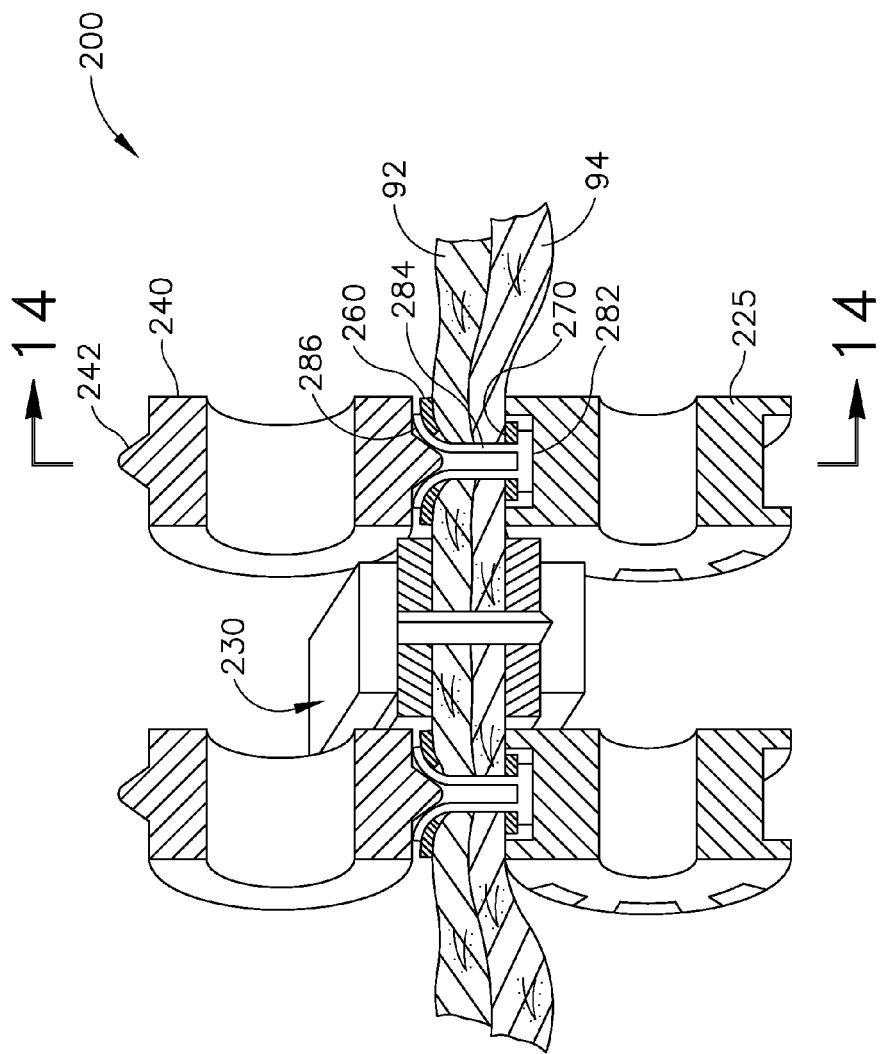
FIG. 13 depicts a cross-sectional end view of an exemplary alternative end effector that may be incorporated into the instrument of FIGS. 1A-1B.
Figure 14:
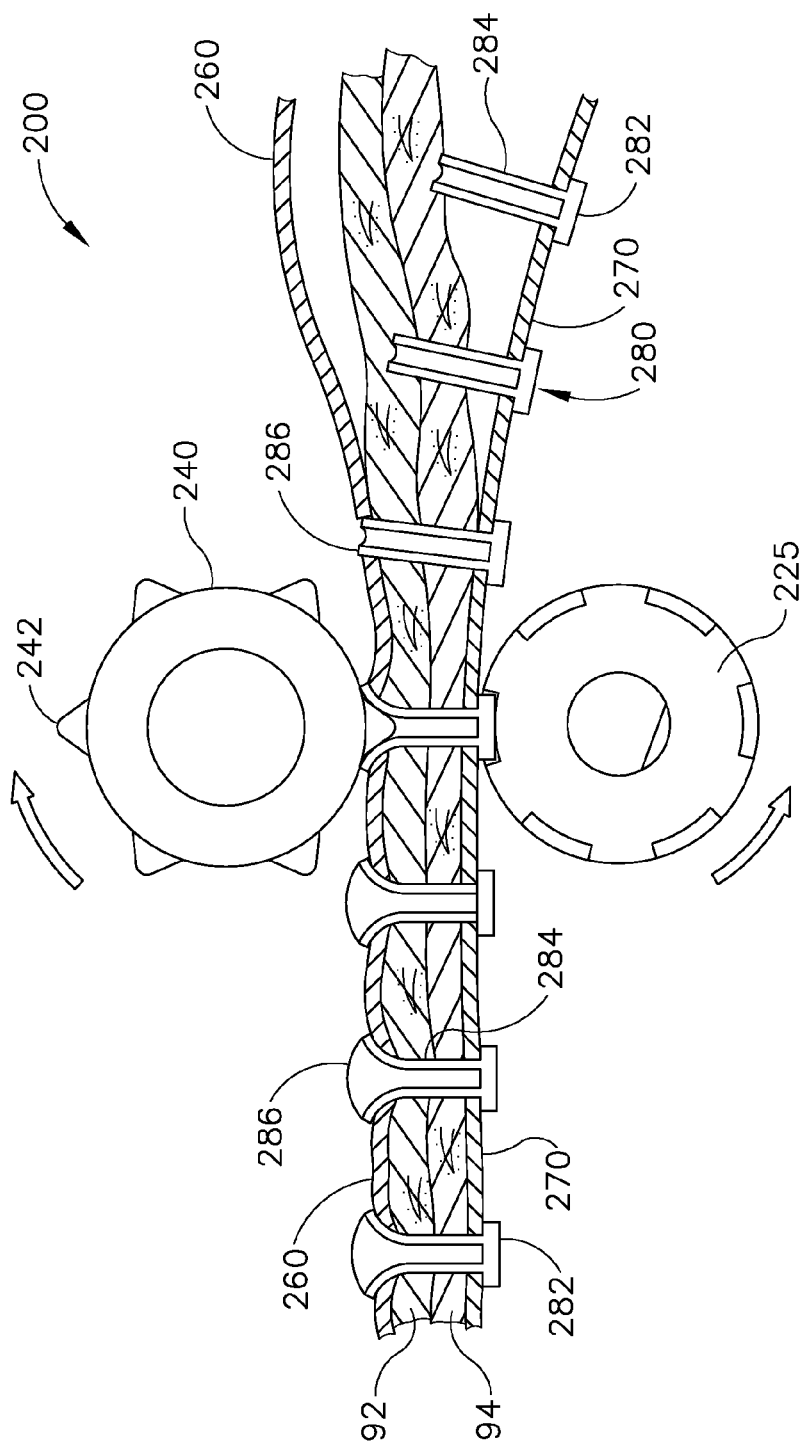
FIG. 14 depicts a cross-sectional side view of the end effector of FIG. 13, taken along line 14-14 of FIG. 13.
Figure 15:
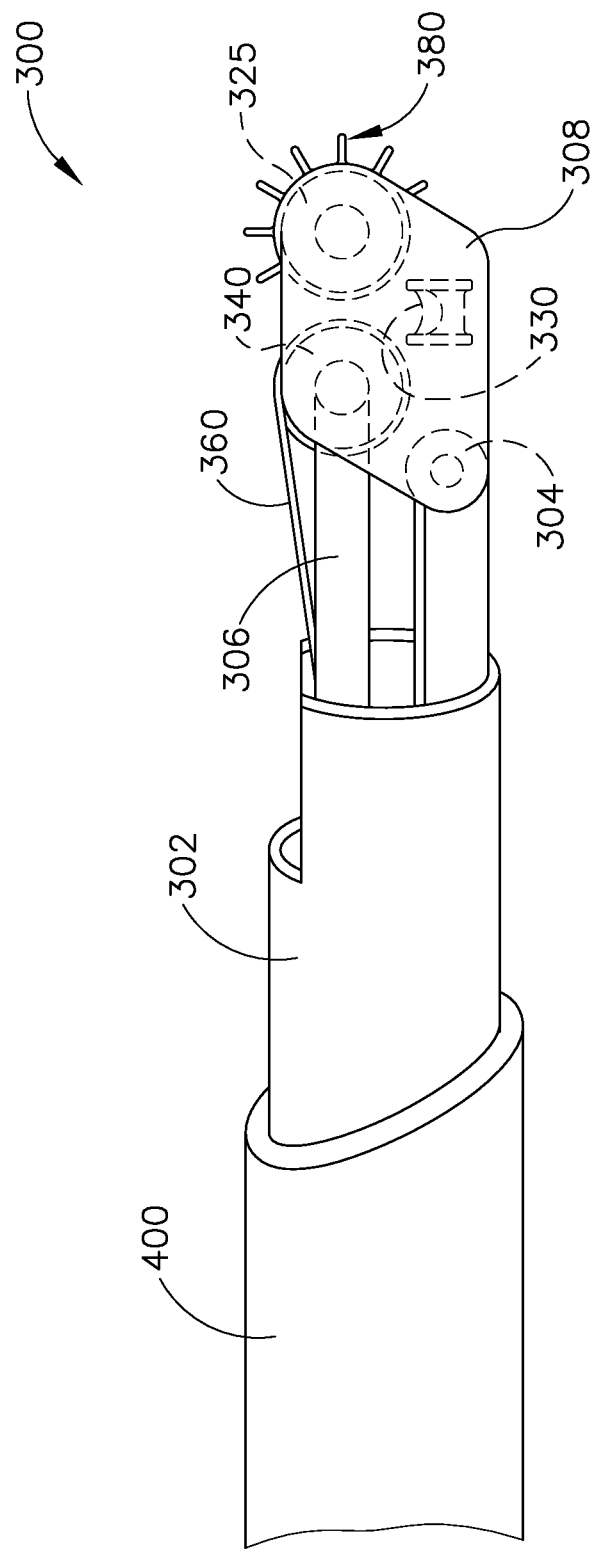
FIG. 15 depicts a side elevational view of another exemplary alternative end effector that may be incorporated into the instrument of FIGS. 1A-1B, disposed through a trocar in a straight configuration.
Figure 16:
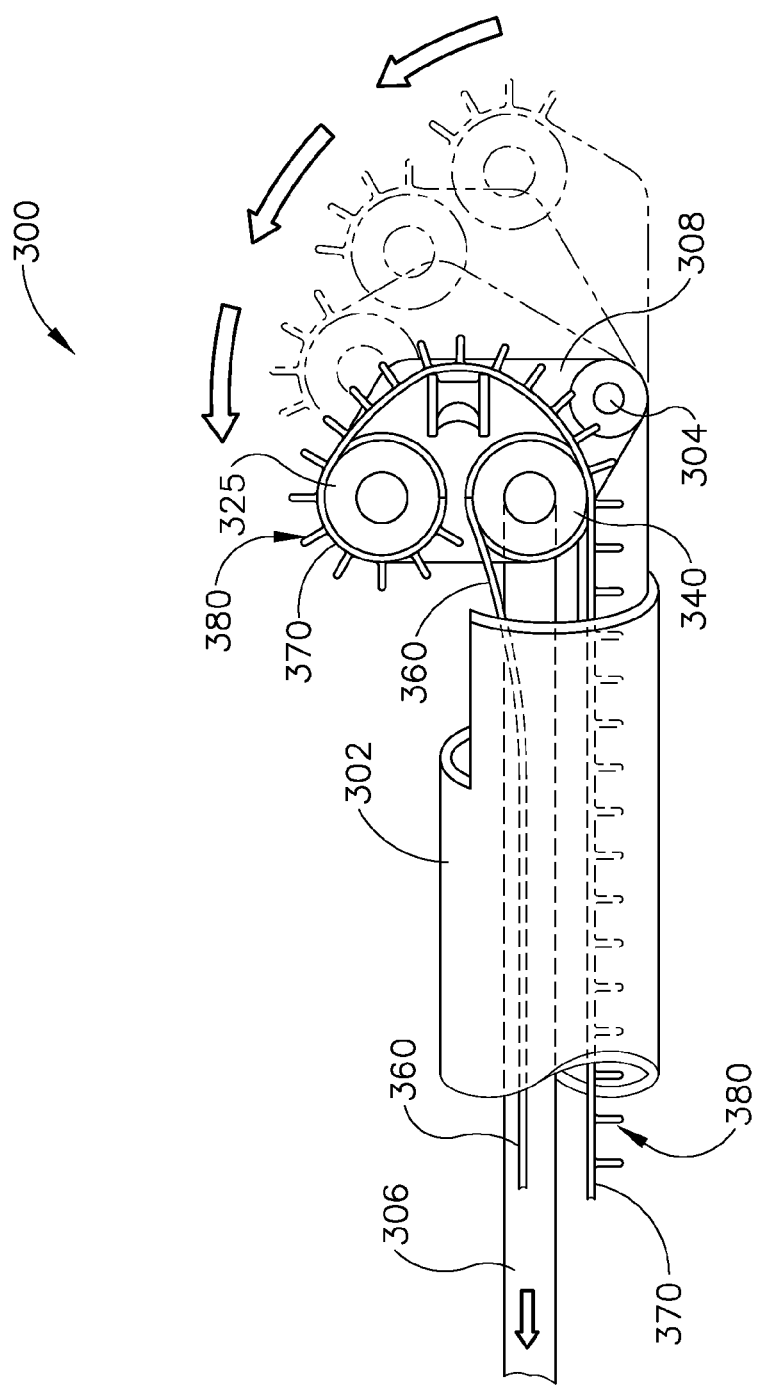
FIG. 16 depicts a side elevational view of the end effector of FIG. 15, pivoted to an angled configuration.

B. Exemplary End Effector for Continuous Stapling with Pivoting Jaw and Rivet Fasteners FIGS. 13-14 show an exemplary alternative end effector (200) that may be used in place of end effector (100) described above. End effector (200) of this example comprises a pair of upper rolling anvils (240) and a pair of lower rolling guides (225). Anvils (240) and guides (225) are provided in opposing pairs, and each pair is positioned on opposing sides of a tissue cutting member (230). It should be understood that anvils (240) may be located in an upper jaw like upper jaw (110); while guides (225) may be located in a lower jaw like lower jaw (120). Anvils (240) are thus similar to anvils (140), with guides (225) being similar to rollers (125) and tissue cutting member (230) being similar to tissue cutting member (130). Anvils (240) and/or guides (225) may be driven by something similar to drive shaft (150), etc. Tissue cutting member (230) may be operable to translate to sever tissue, to vibrate at ultrasonic frequencies to sever and coagulate tissue, and/or to deliver RF energy to tissue, all as described above with respect to tissue cutting member (130). In the present example, tissue cutting member (230) is positioned to cut layers (92, 94) of tissue after the layers (92, 94) are secured by the fastening assembly described below, though it should be understood that tissue cutting member (230) may instead be otherwise positioned.

End effector (200) of the present example is configured to form a fastening assembly with a rivet strip (270), rivets (280), and a buttress strip (260). It should be understood that buttress strip (260) may be viewed as a substitute for buttress strip (160) described above; while rivet strip (270) and rivets (280) may together be viewed as a substitute for wire (170). By way of example only, each strip (260, 270) may be formed of any of the various materials listed above as being suitable for forming buttress strips (160). Various other suitable materials and configurations that may be used for strips (260, 270) will be apparent to those of ordinary skill in the art in view of the teachings herein. It should also be understood that buttress strip (260) may be formed of one material (or combination of materials) while rivet strip (270) is formed of a different kind of material (or combination of materials).

Buttress strip (260) may be fed from a reel or some other kind of source; while rivet strip (270) and rivets (280) may also be fed from a reel or some other kind of source. Each rivet (280) comprises a lower flange (282) and a hollow shaft section (284) with an open free end (286). Rivets (280) are disposed in rivet strip (270), with lower flanges (282) being positioned below rivet strip (270) to prevent rivets (280) from being pulled through rivet strip (270). Rivets (280) are configured for hollow shaft section (284) to penetrate layers (92, 94) of tissue and pass through buttress strip (260). In some instances, buttress strip (260) includes preformed openings that are spaced and configured to receive hollow shaft sections (284). In some other instances, hollow shaft sections (284) form their own openings in buttress strip (260).

After each free end (286) passes through buttress strip (260), anvil (240) deforms free end (286) to form a rivet head on the top of buttress strip (260) as best seen in FIG. 14. In particular, anvil (240) includes spiked projections (242) that extend radially outwardly and that are spaced and configured to enter successive free ends (286) as the fastening assembly is fed between rolling anvil (240) and rolling guide (225). The spiked shaped of projections (242) facilitates entry of projections into free ends (286) and further facilitates the outward spreading of free ends (286) to form rivet heads. Rivets (280) are formed of a malleable material such that formed free ends (286) substantially maintain the rivet head configuration after the rivet heads are formed by projections (242). By way of example only, rivets (280) may be formed of various kinds of metal (e.g., micro-stamped titanium, titanium based alloys, etc.) and/or any other suitable material(s) (e.g., absorbable poliglecaprone (PGCL) such as MONOCRYL by Ehticon, Inc., of Somerville, N.J., etc.). Various other suitable materials that may be used to form rivets (280) will be apparent to those of ordinary skill in the art in view of the teachings herein.

With rivet heads formed at free ends (286) above buttress strip (260) and flanges (282) below rivet strip (270), it should be understood that strips (260, 270) and rivets (280) will cooperate to hold layers (92, 94) of tissue together. It should also be understood that the layers (92, 94) of tissue may be compressed between anvils (240) and guides (225) as the rivet heads are being formed, such that the assembly of strips (260, 270) and rivets (280) holds layers (92, 94) of tissue in a compressed configuration. It should further be understood that such holding of layers (92, 94) may provide hemostasis of the tissue, substantially preventing bleeding of the tissue at the transection cut formed by tissue cutting member (230). As noted above, anvils (240) and/or guides (225) may be driven by something similar to drive shaft (150), etc. Such driven motion of anvils (240) and/or guides (225) may further drive strips (260, 270) relative to tissue, as shown in FIG. 14.

End effector (200) may be operated in a manner similar to the operation of end effector (100) described above. It should also be understood that the above process may be carried out and repeated for as long as desired, enabling the operator to create secured transections having an effectively indefinite length (e.g., especially if a significant amount of strips (260, 270) and rivets (280) is preloaded), without having to remove end effector (200) from the patient. Similarly, the above process may be repeated to create several separate secured transections within the patient, without having to remove end effector (200) from the patient. In instances where the operator is moving from one transection site to another transection site, the operator may simply use a conventional cutting instrument to cut strips (260, 270) before moving to the latter transection site. Still other suitable components, features, configurations, operabilities, and variations that may be associated with end effector (200) will be apparent to those of ordinary skill in the art in view of the teachings herein.

Figure 17:
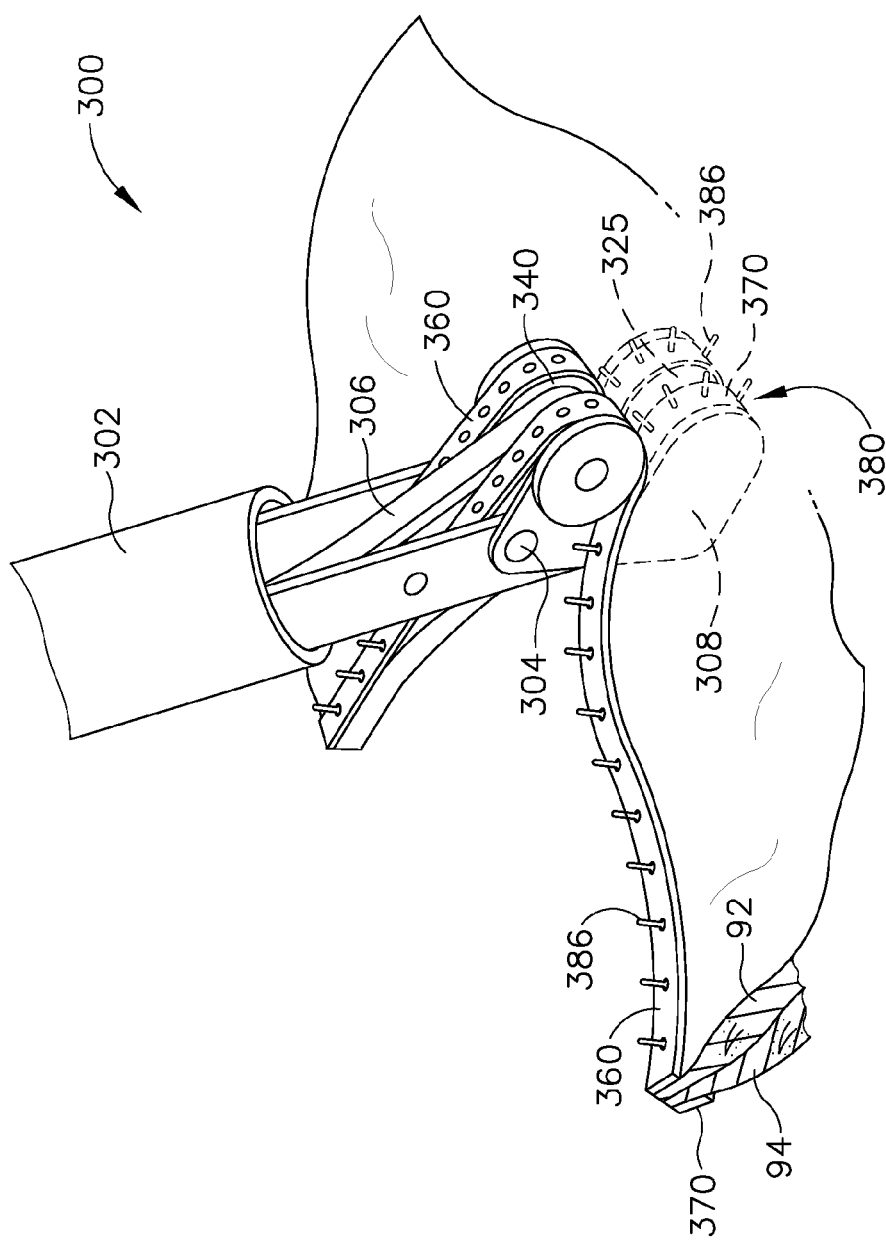
FIG. 17 depicts a perspective view of the end effector of FIG. 15 transecting and tacking tissue.

C. Exemplary End Effector for Continuous Stapling with Pivoting Head and Opposing Rollers FIGS. 15-18 show another exemplary end effector (300) that may be used to provide transection and continuous fastening of tissue, similar to end effectors (100, 200) described above. End effector (300) of this example is disposed at the distal end of a shaft (302). End effector (300) comprises a chassis (308) that is joined to shaft (302) by a pivot pin (304), such that end effector (300) configured to pivot relative to shaft (302) about pivot pin (304) to transition between a straight configuration (FIG. 16) and a pivoted configuration (FIG. 17). When end effector (300) is in a straight configuration, end effector (300) and shaft (302) may be fed through a conventional trocar cannula (400) to reach a surgical site within a patient, in a minimally invasive manner. Once end effector (300) has been positioned within the patient, end effector (300) may then be pivoted relative to shaft (302) as desired to achieve an ideal orientation based on the patient's anatomy and the location of the tissue that is to be transected/fastened. The desired degree of pivoting may vary based on a variety of other factors.

In the present example, end effector (300) is selectively pivoted by translating a band (306) that extends through shaft (302) and is coupled with chassis (308). Band (306) is pulled proximally to transition end effector (300) from the straight configuration to the pivoted configuration. It should be understood that end effector (300) may be oriented at various angles relative to shaft (302) when end effector (300) is in a pivoted configuration. In some versions, end effector (300) is resiliently biased to assume the straight configuration such that band (306) is simply released in order to transition end effector (300) from a pivoted configuration back toward the straight configuration. In some other versions, band (306) is actively pushed distally to transition end effector (300) from a pivoted configuration back toward the straight configuration. Various suitable ways in which band (306) may be actuated will be apparent to those of ordinary skill in the art in view of the teachings herein. Similarly, various other suitable ways in which end effector (300) may be transitioned between a straight configuration and a pivoted configuration will be apparent to those of ordinary skill in the art in view of the teachings herein. By way of example only, a cable, a rack and pinion, a chain drive, and/or various other suitable features may be used in addition to or in lieu of band (306).

End effector (300) further comprises a pair of rolling anvils (340) and rolling guides (325), all of which are rotatably secured to chassis (308). Anvils (340) and guides (325) are arranged similar to anvils (240) and guides (225) as described above. In particular, anvils (340) and guides (325) are provided in opposing pairs, and each pair is positioned on opposing sides of a tissue cutting member (330). Unlike end effectors (100, 200), end effector (300) of this example lacks a pivoting jaw. In some versions, the spacing between anvils (340) and guides (325) is fixed. In some other versions, end effector (300) includes a feature that is operable to vary the spacing between anvils (340) and guides (325). It should also be understood that anvils (340) and/or guides (325) may be rotatably driven relative to chassis (308), such as via drive shaft, via belt, via cable, and/or in any other suitable fashion as will be apparent to those of ordinary skill in the art in view of the teachings herein. Tissue cutting member (330) is configured to cut tissue and may be fixedly secured to chassis (308) or may be operable to move relative to chassis (308). By way of example only, tissue cutting member (330) may be operable to translate to sever tissue, to vibrate at ultrasonic frequencies to sever and coagulate tissue, and/or to deliver RF energy to tissue, all as described above with respect to tissue cutting member (130). In the present example, tissue cutting member (330) is positioned to cut layers (92, 94) of tissue after the layers (92, 94) are secured by the fastening assembly described below, though it should be understood that tissue cutting member (330) may instead be otherwise positioned.

End effector (300) of the present example is configured to form a fastening assembly with a fastener strip (370), fasteners (380), and a buttress strip (360). It should be understood that buttress strip (360) may be viewed as a substitute for buttress strip (160) described above; while fastener strip (370) and fasteners (380) may together be viewed as a substitute for wire (170). By way of example only, each strip (360, 370) may be formed of any of the various materials listed above as being suitable for forming buttress strips (160). Various other suitable materials and configurations that may be used for strips (360, 370) will be apparent to those of ordinary skill in the art in view of the teachings herein. It should also be understood that buttress strip (360) may be formed of one material (or combination of materials) while fastener strip (370) is formed of a different kind of material (or combination of materials).

Buttress strip (360) may be fed from a reel or some other kind of source; while fastener strip (370) and fasteners (380) may also be fed from a reel or some other kind of source. Each fastener (380) comprises a lower flange (382) and a shaft section (384) with a barbed free end (386). Fasteners (380) are disposed in fastener strip (370), with lower flanges (382) being positioned below fastener strip (370) to prevent fasteners (380) from being pulled through fastener strip (370). Fasteners (380) are configured for barbed free ends (386) to penetrate layers (92, 94) of tissue and pass through buttress strip (360). In some instances, buttress strip (360)

includes preformed openings that are spaced and configured to receive barbed free ends (386). In some other instances, barbed free ends (386) form their own openings in buttress strip (360).

Figure 18:
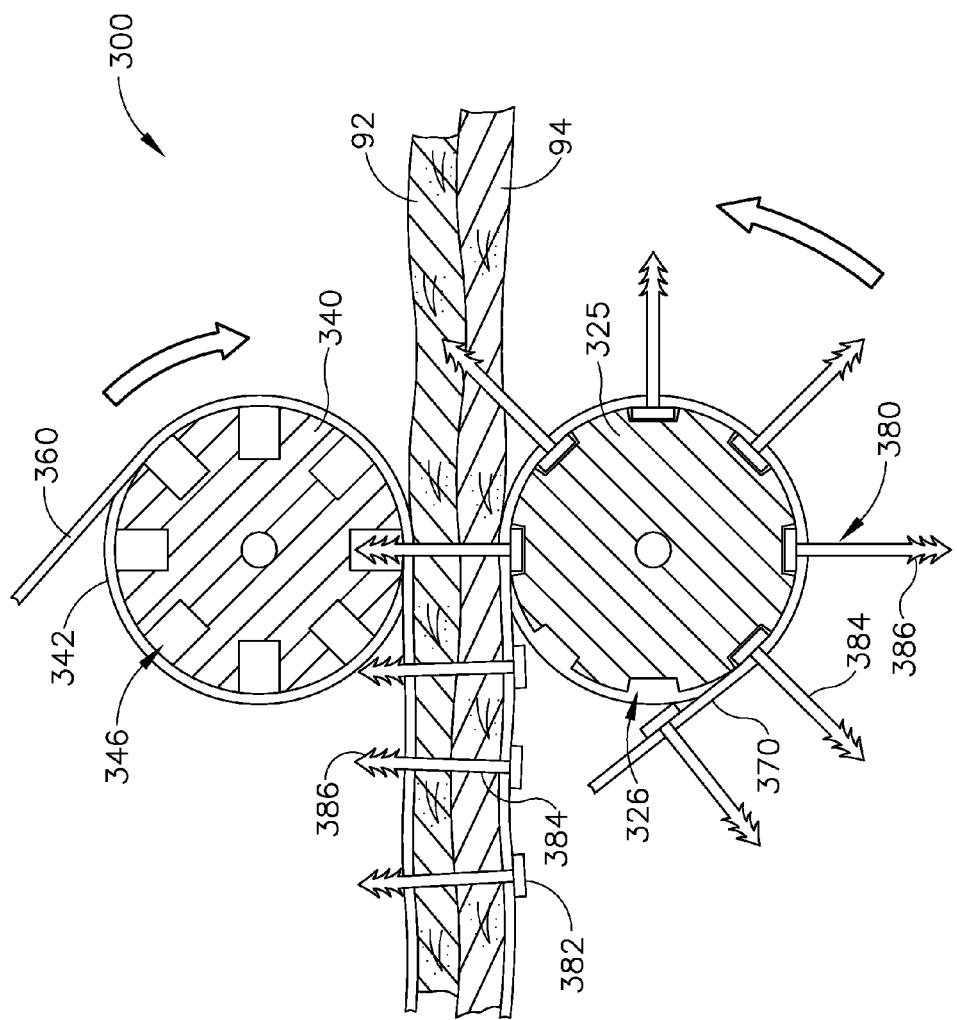
FIG. 18 depicts a cross-sectional side view of the end effector of FIG. 15.

Each anvil (340) includes a pair of radially extending flanges (342) and recesses (346) that are angularly disposed about the perimeter of anvil (340). While eight recesses (346) are shown in the present example, it should be understood that any other suitable number of recesses (346) may be used. Flanges (342) are configured to guide and laterally retain buttress strip (360) relative to anvil (340); while recesses (346) are configured to receive barbed free ends (386) of fasteners (380). In particular, recesses (346) are configured to allow barbed free ends (386) to pass through buttress strip (360), without any resistance being provided by anvil (340). Thus, unlike anvils (140, 240) described above, anvil (340) of the present example does not deform fasteners (380). Guides (325) include recesses (326) that are configured to guide and laterally retain flanges (382) relative to guides (325). Recesses (346, 326) are configured to successively align with each other at the interface of tissue layers (92, 94) during rotation of anvils (340) and guides (325), as shown in FIG. 18. It should be understood that the barbed configuration of barbed free ends (386) substantially prevents barbed free ends (386) from being pulled back through buttress strip (360) after barbed free ends (386) are passed through buttress strip (360). By way of example only, fasteners (380) may be formed of various kinds of metal (e.g., micro-stamped titanium, titanium based alloys, etc.) and/or any other suitable material(s) (e.g., absorbable poliglecaprone (PGCL) such as MONOCRYL by Ehticon, Inc., of Somerville, N.J., etc.). Various other suitable materials that may be used to form fasteners (380) will be apparent to those of ordinary skill in the art in view of the teachings herein.

With barbed free ends (386) above buttress strip (360) and flanges (382) below fastener strip (370), it should be understood that strips (360, 370) and fasteners (380) will cooperate to hold layers (92, 94) of tissue together. It should also be understood that the layers (92, 94) of tissue may be compressed between anvils (340) and guides (325) as the barbed free ends (386) are being driven through layers (92, 94), such that the assembly of strips (360, 370) and fasteners (380) holds layers (92, 94) of tissue in a compressed configuration. It should further be understood that such holding of layers (92, 94) may provide hemostasis of the tissue, substantially preventing bleeding of the tissue at the transection cut formed by tissue cutting member (330). As noted above, anvils (340) and/or guides (325) may be driven to rotate. Such driven motion of anvils (340) and/or guides (325) may further drive strips (360, 370) relative to tissue, as shown in FIG. 18.

End effector (300) may be operated in a manner similar to the operation of end effector (100) described above. It should also be understood that the above process may be carried out and repeated for as long as desired, enabling the operator to create secured transections having an effectively indefinite length (e.g., especially if a significant amount of strips (360, 370) and fasteners (380) is preloaded), without having to remove end effector (300) from the patient. Similarly, the above process may be repeated to create several separate secured transections within the patient, without having to remove end effector (300) from the patient. In instances where the operator is moving from one transection site to another transection site, the operator may simply use a conventional cutting instrument to cut strips (360, 370) before moving to the latter transection site. Still other suitable components, features, configurations, operabilities, and variations that may be associated with end effector (300) will be apparent to those of ordinary skill in the art in view of the teachings herein.

III. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical apparatus, comprising:
   (a) a shaft, wherein the shaft has a distal end;
   (b) an end effector, wherein the end effector is disposed at the distal end of the shaft, wherein the end effector comprises:
      (i) a first jaw having an anvil member, wherein the anvil member is rotatable within the first jaw relative to the first jaw, and
      (ii) a second jaw having a guide member;
   (c) a first fastener assembly member, wherein the anvil is configured to receive the first fastener assembly member, wherein the first fastener assembly member is configured to translate distally through the shaft to be received by the anvil member during rotation of the anvil member; and
   (d) a second fastener assembly member, wherein the guide member is configured to receive the second fastener assembly member;
   wherein the first and second fastener assembly members are configured to join together,
   wherein the anvil is configured to deform a portion of the second fastener assembly member to secure the first and second fastener assembly members together.

2. The surgical apparatus of claim 1, wherein the
   a first jaw and
   second jaw define a gap,
   wherein the first jaw is pivotable relative to the second jaw to selectively vary the gap.

3. The surgical apparatus of claim 1, wherein the first jaw defines a first channel configured to guide the first fastener assembly member toward the anvil, and wherein the second jaw defines a second channel configured to guide the second fastener assembly member toward the guide member.

4. The surgical apparatus of claim 3, wherein the second channel defines a bend configured to redirect the path of the second fastener assembly member from a distal direction to a proximal direction.

5. The surgical apparatus of claim 1, wherein the end effector further comprises a tissue cutting member operable to cut tissue.

6. The surgical apparatus of claim 5, wherein the tissue cutting member is configured to translate relative to the anvil.

7. The surgical apparatus of claim 5, wherein the tissue cutting member is positioned proximally relative to the anvil.

8. The surgical apparatus of claim 1, wherein the anvil defines angularly arrayed recesses configured to deform portions of the second fastener assembly member.

9. The surgical apparatus of claim 1, wherein the anvil defines angularly arrayed protrusions configured to deform portions of the second fastener assembly member.

10. The surgical apparatus of claim 1, wherein the first fastener assembly member comprises a buttress strip.

11. The surgical apparatus of claim 1, wherein the second fastener assembly member comprises a wire, wherein the wire includes malleable protruding portions, wherein the anvil is configured to deform the malleable protruding portions.

12. The surgical apparatus of claim 1, wherein the second fastener assembly member comprises:
    (i) a strip, and
    (ii) a plurality of fasteners extending transversely from the strip, wherein the first fastener assembly member is configured to receive the plurality of fasteners.

13. The surgical apparatus of claim 12, wherein each of the fasteners comprises a deformable free end, wherein the anvil is configured to deform each free end into a rivet head configuration.

14. The surgical apparatus of claim 12, wherein each of the fasteners comprises a barbed free end, wherein the barbed free ends are configured to lock into the first fastener assembly member.

15. The surgical apparatus of claim 1, wherein the entire end effector is pivotable relative to the shaft.

16. The surgical apparatus of claim 1, further comprising:
    (a) a first reel, wherein a portion of the first fastener assembly member is gathered on the first reel; and
    (b) a second reel, wherein a portion of the second fastener assembly member is gathered on the second reel.

17. The surgical apparatus of claim 1, wherein the guide member is a rolling guide.

* * * * *